(12) United States Patent
Livingston et al.

(10) Patent No.: US 8,518,434 B2
(45) Date of Patent: Aug. 27, 2013

(54) ANTISEPTIC SPERMICIDAL COMPOSITION AND MEANS FOR ITS APPLICATION

(75) Inventors: George M. Livingston, Ontario (CA); David B. Thornburgh, Miami Beach, FL (US); Jeffrey Longmore, Houston, TX (US)

(73) Assignee: St. Michael's Medical, Inc., Prescott, AZ (US)

( * ) Notice: Subject to any disclaimer, the term of this patent is extended or adjusted under 35 U.S.C. 154(b) by 1596 days.

(21) Appl. No.: 11/413,309

(22) Filed: Apr. 28, 2006

(65) Prior Publication Data

US 2006/0193822 A1    Aug. 31, 2006

Related U.S. Application Data

(63) Continuation of application No. 10/206,324, filed on Jul. 29, 2002, now abandoned, which is a continuation of application No. 09/995,570, filed on Nov. 29, 2001, now abandoned, which is a continuation of application No. 08/745,192, filed on Nov. 7, 1996, now abandoned, which is a continuation of application No. 08/310,738, filed on Sep. 22, 1994, now abandoned.

(51) Int. Cl.
*A61F 6/06* (2006.01)
*A61F 13/02* (2006.01)
*A61F 13/00* (2006.01)

(52) U.S. Cl.
USPC ............................ 424/430; 424/431; 424/433

(58) Field of Classification Search
USPC .......................................... 424/430, 431, 433
See application file for complete search history.

(56) References Cited

U.S. PATENT DOCUMENTS

| | | | | |
|---|---|---|---|---|
| 3,570,662 A | * | 3/1971 | Polyak | 206/216 |
| 4,321,277 A | * | 3/1982 | Saurino | 514/643 |
| 4,804,674 A | * | 2/1989 | Curtis-Prior et al. | 514/400 |
| 5,354,558 A | * | 10/1994 | Britton et al. | 424/433 |
| 5,387,611 A | * | 2/1995 | Rubinstein | 514/588 |

OTHER PUBLICATIONS

Sangi-Haghpeykar et al., abstract of "Sperm Transport and Survival Post-Application of a New Spermicide Contraceptive," *Contraception*, Jun. 1996, pp. 353-356, vol. 53, Issue 6, Elsevier Inc., accessed and retrieved and online from www.sciencedirect.com on Nov. 6, 2009.

No authors listed, Abstract of "New Advantage 24 Contraceptive Gel Claims 24-Hour Effectiveness. But Proposed FDA Rule Could Put n-9 Products to the Test," *Contraception Technol Update*, Apr. 1995, pp. 45-49, vol. 16, Issue 4, accessed and retrieved and online from www.ncbi.nlm.gov/pubmed/1234706 on Nov. 6, 2009.

Trademark information for "Advantage 24," Serial No. 74362967, accessed and retrieved online via the Trademark Electronic Search System on the USPTO website on Nov. 6, 2009.

Xu et al., "Contraceptive Efficacy of Bioadhesive Benzalkonium Chloride Gel in Comparison With Nonoxynol-9 Gel," *Chin. J. Obstet. Gynecol.* Oct. 2006, vol. 41, No. 10, with English language abstract.

Product information for Advantage 24™, produced by Roberts, website indicates that Advantage 24™ was reviewed in 1997, information submitted was retrieved from RXMED: Pharmaceutical Information, The Comprehensive Resource for Physicians, Drug and Illness Information, which was online at www.rxmed.com on Nov. 6, 2009.

\* cited by examiner

*Primary Examiner* — Shengjun Wang
(74) *Attorney, Agent, or Firm* — Oliff & Berridge, PLC

(57) ABSTRACT

This invention provides a spermicidally and virucidally effective, vaginally applicable formulation, having the following approximate composition of essential ingredients: at least one benzalkonium chloride, in an amount from 0.05 to 0-0.2%; at least one spermicide selected from the group consisting of nonoxynols in an amount of from 0.05-12%, octoxynol-9 in an amount of from 0.05-4%, and triclosan in an amount from 0.05-2%; a biologically acceptable emollient, in an amount from 1-5%; hydroxypropyimethyl cellulose, in an amount from 0.1-3%; sodium carbomer, in an amount from 0.1-1%; de-ionized water, making up the balance. The composition has the attributes of (a) a semi-solid, essentially clear gel consistency and appearance, and (b) the ability to maintain a presence in the human vagina in the presence of mucous secretions therein, in virucidally effective amounts, for at least 24 hours after application thereto.

22 Claims, 1 Drawing Sheet

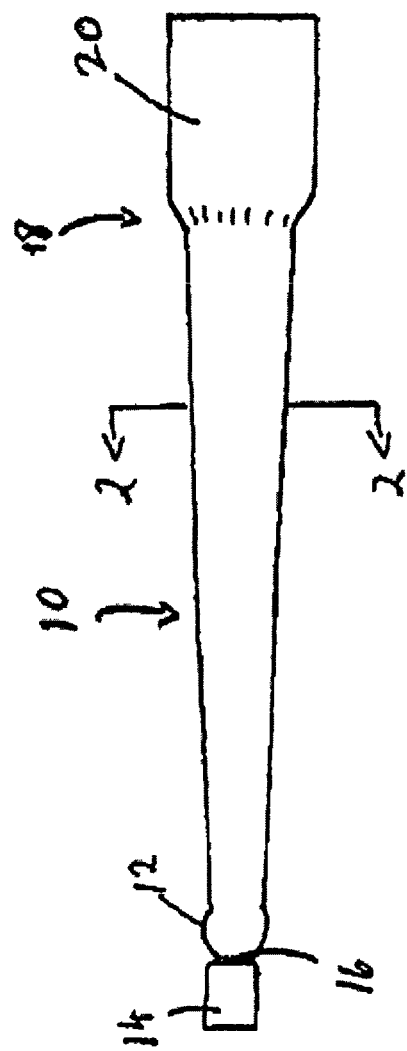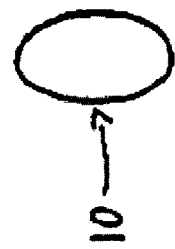
FIG. 1
FIG. 2

ANTISEPTIC SPERMICIDAL COMPOSITION AND MEANS FOR ITS APPLICATION

This application is a continuation of U.S. patent application Ser. No. 10/206,324, filed Jul. 29, 2002 now abandoned, which is a continuation of application Ser. No. 09/995,570, filed on Nov. 29, 2001, now abandoned, which is a continuation of application Ser. No. 08/745,192, filed on Nov. 7, 1996, now abandoned, which is a continuation of application Ser. No. 08/310,738, filed on Sep. 22, 1994, now abandoned, the disclosures of which are incorporated herein by reference.

FIELD OF THE INVENTION

This invention relates to antiseptic spermicidal compositions, and more particularly to antiseptic spermicidal compositions for vaginal application, to protect against transmission of sexually transmitted viruses and other infections, and to protect against conception. It also relates to means for effective application of such compositions.

Transmission of infection from body to body as a result of sexual intercourse is one of the principal ways in which viruses such as herpes 1 and 2, HIV, cytomegalo-virus; hepatitis B and the like, and venereal bacterial diseases such as gonorrhea, chancroid, streptococcus, staphylococcus, gardnerella, mycobacteria, etc are spread. Particularly at risk from such infection transmissions are highly sexually active females, e.g. those engaged in the sex trade, who at the same time run high risks of unwanted pregnancy. To date, the most commonly recommended form of protection against such risks has been the use of latex condoms, optionally in conjunction with a spermicidal lubricant. This however depends upon co-operation of the male partner, and does not provide the female participant with full control over the risks to her own body.

Of particular concern in this regard are conditions in emerging, third-world countries, where the availability condoms and spermicidal or germicidal compositions for use therewith is very restricted. The spread of infectious disease, and population control, are items of especial concern. The problems are complicated by the relative lack of expert medical facilities in many such countries, and the educational level of the population at risk.

Any antiviral and contraceptive system having a chance of being accepted, widely used and effective in such places must therefore be simple to use, by the woman herself, without expert: medical assistance. It should be capable of being applied well in advance of the time when the sexual activity is to take place and to remain effective for a substantial period of time thereafter. Moreover it should be physically and aesthetically pleasant, so that it does not detract unnecessarily from the sexual activity, It is an object of the present invention to provide a novel spermicidally effective and virucidally effective composition for female use.

It is a further object of the invention to provide a kit and method for use of such a composition.

SUMMARY OF THE INVENTION

The present invention provides a clear gel formulation for vaginal application, which is contraceptively effective as a spermicide, and antivirally effective to prevent HIV transmission. A formulation has been found which can be applied to the vaginal walls, and will remain thereon in quantities or concentrations to confer effective protection against HIV reception by the female for at least 24 hours following application, without exhibiting harmful effects to these very sensitive mucous-bearing skin surfaces. The formulation contains a very small amount of a strong disinfectant namely one or more benzalkonium chlorides, and a spermicidal substance such as an octoxynol-9, a nonoxynol, and/or triclosan, along with sodium carbomer and other inert ingredients carefully chosen as to both nature and quantity so as to provide a clear semi-solid gel capable of remaining on the vaginal walls for at least 24 hours after application, in a virucidally effective form.

Thus, according to the present invention, from one aspect, there is provided a spermicidally and virucidally effective, vaginally applicable formulation, having the following approximate composition of essential ingredients:

at least one benzalkonium chloride, in an amount from 0.05 to 0.2%;

at least one spermicide selected from the group consisting of nonoxynols in an amount of from 0.05-12%, octoxynol-9 in an amount of from 0.05-4%, and 5-chloro-2-(2,4-dichlorophenoxy)phenol in an amount from 0.05-2%;

a biologically acceptable emollient, providing appropriate consistency;

hydroxypropylmethyl cellulose, in an amount from 0.1-3%;

sodium carbomer, in an amount from 0.1-1%;

de-ionized water, making up the balance, the formulation further possessing the attributes of (a) a semi-solid, essentially clear gel consistency and appearance, and (b) the ability to maintain a presence in the human vagina along with mucous secretions therein, in virucidally effective amounts, for at least 24 hours after application thereto.

Another aspect of the present invention provides a kit for vaginal self-use by a female patient in protection against contracting viral infection and against conception as a result of normal heterosexual intercourse, said kit comprising a vaginal applicator comprising a vaginally insertable tubular member having a length of about five inches, and having an aperturable distal end adapted to be positioned adjacent to the patient's cervix when the applicator is fully inserted into the patient's vagina, and at least one unit dose of the spermicidally and virucidally effective formulation described above, said unit dose being from about 5-10 mls thereof In the accompanying drawings:

FIG. 1 is a side view of an applicator for use in the kit of the present invention;

FIG. 2 is a cross sectional view of the applicator of FIG. 1, along the line 1-1 of FIG. 1.

The benzalkonium chlorides used in the present invention are known compounds, many of which have previously been sold and used for disinfecting purposes in non-skin contacting applications. Thus, they are sold for purposes of making up a disinfectant wash solutions for floors, walls, operating surfaces and the like, but always with strong warnings to avoid skin contact with them if at all possible. They are powerful poisons and skin irritants, as well as powerful disinfectants. The present invention takes advantage of the fact, hitherto unreported, that they will destroy harmful viruses such as herpes simplex types 1 and 2 and HIV when they are present in formulations in such low concentrations that they acceptable on and non-harmful to the human vaginal walls. These viruses in fact are not difficult to kill when encountered in isolation in external body fluids or secretions. It is after they have infected the mammalian body and become to replicate in the body cells that they become almost impossible to treat effectively. If the viruses can be caught and treated on transmission from body to body, they are vulnerable to common disinfectants such as those used in the compositions of the present invention.

To safeguard against risks of skin irritation, the benzalkonium chloride is preferably used in the composition of the present invention in amounts from 0.05-0.121% by weight. Specific examples of benzalkonium chlorides for use in the present invention include alkyl dimethyl benzyl ammonium chloride and alkyl dimethylethylbenzyl ammonium chloride, in which the alkyl portions are $C_{12}$-$C_{18}$ in length, and mixtures thereof, and myristylbenzalkonium chloride. Such a suitable mixture is available commercially under the trade name MAQUAT MQ2525M—50%, from Mason Chemical Comany, Chicago, Ill., and under the trade name BTC 2125M from Stepan Company, North Field, Ill.

Compositions according to the present invention also include a small but effective amount of a spermicide. The spermicide is selected from nonoxynols, octoxynol-9 and triclosan (which is, chemically, 5-chloro-2-(2,4-dichlorophenoxy)phenol)), and are used in the amounts set out above. The octoxynol series are polyethylene glycol p-isooctylphenyl ethers such as octoxynol-9 (Triton X-100). The nonoxynol series are polyoxyethylene nonylphenyl ethers, of various numbers of ethylene oxide units, e.g.—is nonoxynol 9 and nonoxynol 10 They also confer surfactant properties on the compositions of the invention, making them easier to spread over the surface of the vaginal walls.

Whilst the various additional ingredients added to the composition of the present invention are in a sense carriers, in that they are not virucidally or spermicidally active, they nevertheless play important roles in determining the nature and thereby rendering the compositions acceptable for use. The combination of the emollient (which is preferably glycerine), sodium carbomer and hydroxypropylmethyl cellulose in the specified relative amounts in the formulation of the invention ensures a semi-solid clear gel composition, which is a very important factor in the acceptability of the composition for its intended use. Opaque, coloured compositions will not gain consumer acceptance for vaginal use as a protectant against sexually transmitted infections.

Even more important is the fact that the composition of the invention has its inert ingredients selected and present in amounts which ensure a gel which is long lasting in its effectiveness after application. The combination of the hydroxypropylmethyl cellulose and the sodium carbomer in the specified proportions ensures a composition of sufficient adherence to the patients' vaginal walls that it remains effective against HIV transmission for at least 24 hours. Accordingly the patient needs only a single daily self-application of the composition of the present invention, to obtain the required protection. She has total and sole control over this protection for herself, without reliance on partners or medical practitioners.

The composition of the present invention contains one or more emollients such as glycerine, lanolin, aloe vera, paraffin oils, glycerol monostearate, myrj compounds, Tween, PEG compounds, sodium lauryl sulphate, etc., and mixtures of two or more of them, to improve the lubricity and general oiliness of the composition. Glycerine is the preferred emollient. It can also if desired contain various perfumes. Any ingredients which are used must be skin compatible, inert towards the active ingredients, and of a nature and used in an amount which does not destabilize or upset the general consistency of the formulation.

Sodium carbomer used as a key ingredient in the composition of the present invention to provide the necessary consistency for long lasting (minimum 24 hour) action, is a known substance. It is the sodium salt of carbopol, which in turn is a polymer of acrylic acid having free carboxyl groups, which is dispersed in water to form a slight gel. Then a suitable water soluble base such as sodium hydroxide is added, forming a salt and affecting the conformation of the polymer in solution and causing high gelling effect. Various grades of carbopol are available, having different acid values and molecular weights.

The formulations according to the present invention can be prepared using standard cosmetic or pharmaceutical gel formulating procedures and equipment. There is no particular, critical order of addition of components, mixing temperatures or the like, provided that a homogeneous, reasonably stable end product is achieved.

The composition of the present invention is useful as a spermicide and antiseptic, alone or in combination with a condom or a diaphragm. It is a topical intravaginal gel which is water soluble but has the property of remaining in the vagina for extended periods of time. It helps protect against the transmission of various sexually transmitted diseases such as viral (HIV or AIDS, herpes, hepatitis B cytomegalovirus), chlamydia, trichomonas, various bacteria including gonorrhea and G. Vaginalis and test strain of *Treponema phagedenis*, a surrogate for syphilis. It is not harmful to epithelium but will destroy lymphocytes and macrophages which carry the AIDS virus or HIV in persons infected with AIDS.

The composition of the present invention is specially formulated for vaginal self-application by females. The female adult vagina is normally about five inches in length, and it is important that, for maximum effectiveness, the composition be disposed all the way along the vaginal wall, and particularly at the inner end thereof, adjacent to the cervix. Accordingly, a preferred embodiment of the present invention provides the composition as described above in combination with an applicator which the patient can use to ensure proper application of composition to the most beneficial location. The applicator is a vaginally insertable elongated object about five inches in length, adapted to receive and dispense the formulation. In one preferred embodiment, the applicator is a once usable tube containing a single dosage of formulation, and has an aperture, preferably equipped with a rupturable removable cap, provided at the distal end thereof, i.e. the end to be disposed adjacent to the patient's cervix on full and proper insertion into the vagina. The internal volume of the tubular applicator is about 8.5 ml, which allows discharge of the appropriate dosage of composition to be administered. Normally about 5 ml of formulation should be discharged. The remainder remains in, and is discarded with, the applicator. Another form of applicator is equipped with a plunger which can be operated to empty the internal cavity of the tube through the distal end opening. The tube is filled with the appropriate dosage of composition, inserted fully into the vagina, and the plunger is operated to empty it as it is withdrawn therefrom. The length of the applicator ensures that an effective amount of the composition is disposed at the cervical end of the vagina, for maximum protection.

The specific, most preferred formulation for use in the present invention has the following composition (percentages by weight):

| | |
|---|---|
| Carbopol 934P | .40% |
| sodium hydroxide | 0.10% |
| hydroxypropylmethyl cellulose K4M | 1.50% |
| Glycerin | 2.27% |

| | |
|---|---|
| Triton X-100 (octoxynol-9) | 0.20% |
| Benzalkonium chloride (MQ 2525-50%) | 0.20% |
| Water | balance to 100% |

The accompanying drawings diagrammatically illustrate an applicator for use with compositions of the present invention. The apparatus is an elongated tube of total length about 5 inches, having an oval shape as seen in cross section (FIG. 2) On the distal end 12 is a removable or rupturable cap 14 covering an aperture 16. The internal cavity is filled with clear gel composition according to the invention, a quantity of about 8.0 ml. On the proximal end 18 is an integral squeezable reservoir 20, which is used to discharge the contents into the patient's vagina after full insertion of the device into the patient's vagina. The device is factory filled with a single dosage, sealed at the factory, and used once and discarded.

The invention is further described and illustrated in the following specific, non limiting examples.

EXAMPLE 1

A clear gel formulation according to specific, most preferred embodiment of the invention as detailed above was made. The preparation was made by simple mixing of ingredients in a container, at room temperature. Three normal female volunteers agreed to instill 5 ml of the formulation intravaginally and retrieve samples of vaginal secretions from the deep lateral wall of the vagina at varying intervals up to eight hours after instillation. One subject submitted samples eight hours after sexual intercourse (confirmed microscopically). The various samples were assessed for anti-HIV inhibitory activity.

All specimens, even when diluted 10:1, showed excellent activity in subsequent standard in vitro tests against HIV-1. The similar use of a composition of the same active ingredients but omitting the sodium carbomer, and hence having a lotion-like consistency rather than the semisolid gel consistency of the compositions of the invention, yielded a secretion sample which had adequate activity for a short period of time, but at eight hours did not show such activity. Also, the volunteer who used it complained that it rapidly drained from the vagina.

EXAMPLE 2

This experiment was conducted to determine the length of time that the composition of the invention, as used in example 1 above, instilled vaginally, will render vaginal secretions sterile to HIV.

Two HIV seropositive females with previously detectable HIV from vaginal fluids by culture and RNA PCR were selected and studied. Both women had histories of frequent sexual activity and intravenous drug use, T4 counts >200/cu, mm and were known to be HIV infected for greater than 5 years. 1-2 ml of vaginal secretions were aspirated with a pipette from the posterior fornix and vaginal secretions were obtained for HIV studies. HIV RNA PCR and HIV cultures were performed in the standard manner (MT-2 syncytium-inhibition assay). 5.5 ml of the composition of the invention was instilled into the posterior fornix and the women were asked to maintain normal daily activities and to refrain from sexual intercourse. The women were not menstruating. Prior to the installation of the composition and after 8 and 24 hours from installation, samples were obtained for HIV studies.

In both patients with previously detectable HIV by cultures and RNA from cervical secretions, no virus was detected for 24 hours after the application of the composition. It can thus be concluded that the composition of the invention, when administered as described herein, is capable of maintaining vaginal secretions sterile to HIV for at least 24 hours.

The invention claimed is:

1. A spermicidally and virucidally effective vaginally applicable formulation, comprising:
   0.40% carbopol,
   0.10% sodium hydroxide,
   1.50% hydroxypropylmethyl cellulose,
   2.27% glycerin,
   0.20% octoxynol-9,
   0.20% benzalkonium chloride, and
   de-ionized water, making up the balance.

2. The formulation of claim 1, further comprising an inert ingredient.

3. A kit for vaginal self-use by a female patient in protection against contracting viral infection and against conception as a result of normal heterosexual intercourse, said kit comprising a vaginal applicator comprising a vaginally insertable tubular member having a length of about five inches, and having an aperturable distal end adapted to be positioned adjacent to the patient's cervix when the applicator is fully inserted into the patient's vagina, and at least one unit dose of a spermicidally and virucidally effective gel formulation made by combining ingredients consisting essentially of: 0.40% carbopol, 0.10% sodium hydroxide, 1.50% hydroxypropylmethyl cellulose, 2.27% Glycerin, 0.20% octoxynol-9, 0.20% benzalkonium chloride, and de-ionized water, making up the balance, wherein the formulation possesses the attributes of (a) a semi-solid, essentially clear gel consistency and appearance, and (b) the ability to maintain a presence in the vagina of an HIV seropositive woman, along with mucous secretions therein, in virucidally effective amounts, for at least 24 hours after application thereto.

4. The kit of claim 3 wherein the applicator has a squeezable reservoir containing said formulation, in communication with said tubular member.

5. The kit of claim 3 wherein the benzalkonium chloride is selected from the group consisting of alkyl dimethylbenzyl ammonium chloride with alkyl groups of $C_{12}$-$C_{26}$ in length, alkyl dimethylethylbenzyl ammonium chloride with alkyl groups of $C_{12}$-$C_{26}$ in length, mixtures thereof and myristylbenzalkonium chloride.

6. The kit of claim 3, wherein the at least one unit dose is from about 5-10 ml.

7. The kit of claim 6, wherein the at least one unit dose is about 5 ml.

8. A kit for vaginal self-use by a female patient in protection against contracting viral infection and against conception as a result of normal heterosexual intercourse, said kit comprising a vaginal applicator comprising a vaginally insertable tubular member having a length of about five inches, and having an aperturable distal end adapted to be positioned adjacent to the patient's cervix when the applicator is fully inserted into the patient's vagina, and at least one unit dose of a spermicidally and virucidally effective gel formulation comprising:
   0.40% carbopol,
   0.10% sodium hydroxide,
   1.50% hydroxypropylmethyl cellulose,
   2.27% Glycerin, 0.20% octoxynol-9,
   0.20% benzalkonium chloride, and
   de-ionized water, making up the balance.

9. The kit of claim 8, further comprising an inert ingredient.

10. The kit of claim 8, wherein the at least one unit dose is from about 5-10 ml.

11. The kit of claim 10, wherein the at least one unit dose is about 5 ml.

12. A spermicidally and virucidally effective vaginally applicable formulation, made by combining ingredients consisting essentially of: 0.40% carbopol, 0.10% sodium hydroxide, 1.50% hydroxypropylmethyl cellulose, 2.27% Glycerin, 0.20% octoxynol-9, 0.20% benzalkonium chloride, and de-ionized water, making up the balance, wherein the formulation possesses the attributes of (a) a semi-solid, essentially clear gel consistency and appearance, and (b) the ability to maintain a presence in the vagina of an HIV seropositive woman, along with mucous secretions therein, in virucidally effective amounts, for at least 24 hours after application thereto.

13. The formulation of claim 12 wherein the benzalkonium chloride is selected from the group consisting of alkyl dimethylbenzyl ammonium chloride with alkyl groups of $C_{12}$-$C_{18}$ in length, alkyl dimethlethylbenzyl ammonium chloride with alkyl groups of $C_{12}$-$C_{18}$ in length, mixtures thereof and myristylbenzalkonium chloride.

14. The formulation of claim 12 wherein the benzalkonium chloride is selected from the group consisting of alkyl dimethylbenzyl ammonium chloride with alkyl groups of $C_{12}$-$C_{26}$ in length, alkyl dimethylethylbenzyl ammonium chloride with alkyl groups of $C_{12}$-$C_{26}$ in length, mixtures thereof and myristylbenzalkonium chloride.

15. The method of protect against conception and transmission of sexually transmitted viruses, disease bacteria and other infections through sexual contact, comprising:
topically applying a gel formulation of claim 12 to a participant in said sexual contact.

16. The method of claim 15, wherein said gel formulation is applied into a vagina of a human female from a container.

17. The method of claim 16, further comprising:
maintaining the amount of said spermicidally and virucidally effective amount of said gel formulation in said vagina for at least 24 hours.

18. The method of claim 17, comprising applying a single daily application of the gel formulation of claim 12 that maintains the amount of said spermicidally and virucidally effective amount of said formulation in said vagina for at least 24 hours.

19. The method of claim 18, wherein said human female is HIV seropositive.

20. The method of claim 15, wherein the sexually transmitted viruses, disease bacteria and other infections is selected from the group consisting of AIDS, HIV, herpes simplex types 1 and 2, cytomegalo-virus, hepatitis B cytomegalovirus, gonorrhea, syphilis, chancroid, streptococcus, staphylococcus, gardnerella, mycobacteria, chlamydia, trichomonas, Treponema phagedenic, and lymphocytes and macrophages that carry HIV in persons infected with HIV.

21. A method of protect against conception and transmission of sexually transmitted viruses, disease bacteria and other infections through sexual contact, comprising:
opening the distal end of the applicator of the kit of claim 3; and
discharging the gel formulation from the applicator into a participant in said sexual contact.

22. The method of claim 21, wherein said gel formulation is discharged into a vagina of a human female.

* * * * *